United States Patent
Lali et al.

(10) Patent No.: US 9,862,980 B2
(45) Date of Patent: Jan. 9, 2018

(54) PROCESS FOR PRODUCTION OF SOLUBLE SUGARS FROM BIOMASS

(71) Applicants: Department of Biotechnology, New Delhi (IN); Institute of Chemical Technology, Mumbai (IN)

(72) Inventors: Arvind Mallinath Lali, Mumbai (IN); Annamma Anil Odaneth, Mumbai (IN); Sachinkumar Hiraman Birhade, Mumbai (IN); Juliet Joanna Victoria, Mumbai (IN); Sneha Chandrakant Sawant, Mumbai (IN)

(73) Assignees: Department of Biotechnology, New Delhi (IN); Institute of Chemical Technology, Maharashtra (IN)

( * ) Notice: Subject to any disclaimer, the term of this patent is extended or adjusted under 35 U.S.C. 154(b) by 0 days.

(21) Appl. No.: 15/112,089

(22) PCT Filed: Jan. 16, 2015

(86) PCT No.: PCT/IB2015/000034
§ 371 (c)(1),
(2) Date: Jul. 15, 2016

(87) PCT Pub. No.: WO2015/107415
PCT Pub. Date: Jul. 23, 2015

(65) Prior Publication Data
US 2016/0333382 A1   Nov. 17, 2016

(30) Foreign Application Priority Data
Jan. 16, 2014   (IN) .............. 154/MUM/2014

(51) Int. Cl.
*C12P 19/02*   (2006.01)
*C12P 19/12*   (2006.01)

(52) U.S. Cl.
CPC .............. *C12P 19/02* (2013.01); *C12P 19/12* (2013.01); *Y02P 20/582* (2015.11)

(58) Field of Classification Search
CPC ................................ C12P 19/02; C12P 19/12
USPC ........................................................ 435/100
See application file for complete search history.

(56) References Cited

U.S. PATENT DOCUMENTS

| 2009/0053777 A1 | 2/2009 | Hennessey et al. | |
| 2010/0255554 A1* | 10/2010 | Benson | C12P 7/10 435/165 |
| 2013/0344543 A1* | 12/2013 | Kurihara | C13K 1/02 435/99 |

OTHER PUBLICATIONS

Meissner et al., "Optimized enzyme cocktails for the digestion of corn stover", Parker Poster—Agrivida (2010).
Srinorakutara et al., "Effect of Lignocellulosic Substrate and Commercial Cellulase Loading on Reducing Sugar Concentration for Ethanol Production", Journal of Food Science and Engineering 2, 149-156 (2012).
Moreira et al., "The Hydrolysis of Agro-Industrial Residues by Holocellulose-Degrading Enzymes", Brazilian Journal of Microbiology, 498-505 (2012).
Ghose, "Measurement of Cellulase Activities", Pure & Appl. Chem., 59:257-268 (1987).
Pasha et al., "Sequential cellulase production, saccharification and ethanol fermentation using rise straw", Journal of Scientific & Industrial Research, 71:616-620 (2012).
Lynd et al., "Microbial Cellulose Utilization: Fundamentals and Biotechnology", Microbiology and Molecular Biology Reviews, 66:506-577 (2002).
Boonwong et al., "Agricultural Wastes Potential (Pineapple Crown, Durian Peel and Sugarcane Leaves) on Reducing Sugar Production by Using Sulfuric Acid Pretreatment Following Enzymatic Hydrolysis", KKU Res. J., 19(3): 361-369 (2014).
Takahaski et al., "Effect of agitation speed on enzymatic saccharification of dry-pulverized lignocellulosic biomass", Renewable Energy, 62:754-760 (2014).

* cited by examiner

*Primary Examiner* — Scott Long
*Assistant Examiner* — Paul Martin
(74) *Attorney, Agent, or Firm* — Marshall, Gerstein & Borun LLP

(57) ABSTRACT

The present invention provides a process for enzyme mediated hydrolysis of biomass for production of soluble sugars, wherein the said process comprises of steady addition of small portions of biomass to enzyme solution, enabling rapid solubilization of biomass. The process used for enzymatic saccharification allows for increased biomass loading, enzyme recycle and mitigation of substrate and product inhibitory effect. The recycling of unhydrolysed biomass along with soluble enzyme ensures complete reuse of the said enzyme for effective repeated hydrolysis thereby increasing the overall productivity of enzyme used.

12 Claims, 1 Drawing Sheet

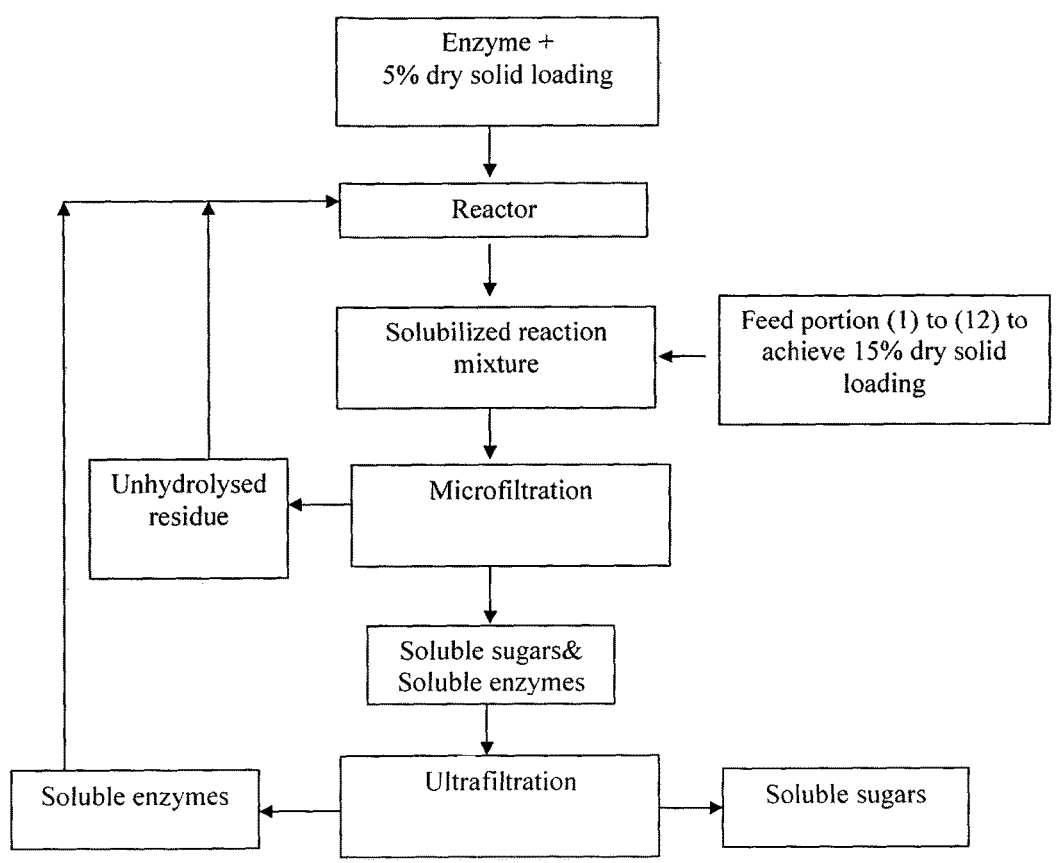

PROCESS FOR PRODUCTION OF SOLUBLE SUGARS FROM BIOMASS

FIELD OF INVENTION

The present invention relates to a process for production of soluble sugars from biomass which is further used to produce valuable products such as fuels and other chemicals, including ethanol.

BACKGROUND OF THE INVENTION

Although biomass has long shown promise as a renewable source of fuel energy, there remains a need for more efficient means of transforming biomass into suitable biofuels. Cellulosic and lignocellulosic feedstocks and wastes, such as agricultural residues, wood, forestry wastes, sludge from paper manufacture, and municipal and industrial solid wastes, provide potential renewable feedstock for the production of valuable products such as fuels and other chemicals. The plant materials are also a significant source of fermentable sugar, such as glucose that can be transformed into biofuels. The sugars in plant material are composed of long chain of polymers comprising cellulose, hemicellulose, glucans and lignin. Thus it is necessary to break down these polymers into monomer sugars. The methods of converting biomass into fermentable sugars are known in the art and in general comprise of two main steps: a pretreatment step to loosen the plant structure, and a chemical or an enzymatic hydrolysis step to convert the polymeric chains of cellulose and hemicellulose into monomeric sugars, which can then be fermented to useful products.

The pretreatment step is a fine balancing act aimed at opening the fibre to enable enzyme accessibility while minimizing sugar loss and inhibitor generation to ensure high yields and substrate suitable for enzymatic hydrolysis and fermentation. Pretreatment methods are used to make the carbohydrate polymers of cellulosic and lignocellulosic materials more readily amenable to saccharification/hydrolysis enzymes.

The pretreated mixture is then subjected to enzymatic hydrolysis using enzyme such as hemicellulases and cellulases, which catalyze the hydrolysis of hemicellulose or cellulose to oligosaccharides and/or monosaccharides in the hydrolysate. The hydrolysate is further subjected to fermentation to produce biofuels. Saccharification enzymes used to produce fermentable sugars from pretreated biomass typically include one or more glycosidases, such as cellulose-hydrolyzing glycosidases, hemicellulose-hydrolyzing glycosidases, starch-hydrolyzing glycosidases, as well as peptidases, lipases, ligninases and/or feruloyl esterases. Saccharification enzymes and methods for biomass treatment are reviewed in Lynd, L. R. et al. (*Microbiol. Mol. Biol. Rev.* (2002) 66:506-577).

US20090053777 discloses a process for saccharification of pretreated biomass to obtain high concentrations of fermentable sugars. The fed batch reactor system includes multiple size reduction steps and mixing to maintain through mixing in a vertical, agitated tank. The process comprises of: providing a portion of mixable pretreated biomass slurry; & portion of saccharification enzyme consortium comprising at least one enzyme capable of hydrolyzing cellulose; reacting said slurry and enzyme at temperature ranging from 25° C. to 60° C. and pH 4.5 to 6.0; applying the article size reduction mechanism; adding an additional portion of pretreated biomass producing a higher solid biomass slurry; reacting said higher solid biomass slurry under same mentioned conditions, wherein repeating the step two more times to produce a high sugar content hydrosylate; where the dry weight of pretreated biomass is in between 24% to 30% to obtain 20% of the weight of the final hydrosylate product.

WO2011157427 describes a continuous process for enzymatic hydrolysis of cellulosic biomass, wherein the process involves addition of predetermined amount of cellulosic biomass and enzyme in a continuously stirred tank reactor to partial enzymatic hydrolysis of cellulosic biomass, wherein the partially hydrolysed cellulosic biomass is continuously removed. The said cellulosic biomass has a solid content in between 10 to 45%.

WO2006063467 discloses a continuous process system for enzymatic hydrolysis of pre-treated cellulose which comprises: introducing aqueous slurry of the pre-treated cellulosic feedstock at the bottom of a vertical column hydrolysis reactor. Axial dispersion in the reactor is limited by avoiding mixing and maintaining an average slurry flow velocity of about 0.1 to about 20 feet per hour, such that the undissolved solids flow upward at a rate slower than that of the liquid. Cellulase enzymes are added to the aqueous slurry before or during the step of introducing the aqueous slurry into the reactor. An aqueous stream comprising hydrolysis products and unhydrolyzed solid is separated and unhydrolyzed cellulose is recycled in same reactor. It also describes the enzyme compositions comprising of cellulase enzymes and flocculents to provide exposure of the enzyme to the substrate for hydrolysis process. The time required for cellulose conversion to glucose is 48 to 200 hrs at respective enzyme loading of 32 units/g cellulose to 5 units/g cellulose.

US20100255554 discloses a method for optimization of a fed batch hydrolysis process wherein the hydrolysis time is minimized by controlling the feed addition of volume and/or batch addition frequency or prehydrosylate and enzyme feed. The mentioned process comprises: filling a reactor vessel with water; adding cellulase enzyme; and sequentially adding lignocellulosic prehydrosylate biomass feed into reactor vessel to produce a reaction mixture, whereby prehydrosylate feed is added in batches at a preselected batch volume and batch addition frequency over a total feed time of 20 hrs to achieve a preselected final consistency and preselected dry matter content in a final reaction mixture. 70 to 90% of a theoretical cellulose to glucose conversion is reached in the reaction mixture, wherein batch addition frequency is one batch every 80 to 105 mins, preselected final consistency is 24%, total feed time is 80 to 120 hrs.

According to the methods described in the prior art the major strategy used in the biofuels production includes three main steps i.e. biomass treatment, enzymatic hydrolysis, and fermentation of sugars to produce biofuels. The main obstacles faced during enzymatic hydrolysis are low rate of reaction, high cost of enzyme, low product concentration. As per the methods described in the prior art, the above described problems is overcome by operating the enzymatic hydrolysis using high insoluble solid consistency. However, the saccharification reaction at high insoluble solid consistency will have to encounter challenges of increased viscosity, higher energy requirement for mixing, shear activation of enzyme and poor heat transfer due to rheological properties of dense fibrous suspension. Thus there is a need to develop a process which can overcome the above challenges.

SUMMARY OF THE INVENTION

One of the aspects of the present invention is to provide a process for enzyme mediated hydrolysis of biomass for production of soluble sugars, wherein the said process comprises of steady addition of small portions of biomass to enzyme solution, enabling rapid solubilization. This enables addition of biomass so as to have high concentrations of substrate in the reaction mixture, enabling efficient saccharification at high substrate loading. The recycling of unhydrolysed biomass along with soluble enzyme ensures complete reuse of the said enzyme for repeated hydrolysis thereby increasing the overall productivity of the enzyme used.

Another aspect of the present invention is to provide a process for production of soluble sugars from biomass, wherein said process comprises: preparing an enzyme solution with pH in the range of 4 to 6 in a reactor vessel at a temperature in the range of 40 to 60° C.; adding one lot of biomass with holocellulose percentage (%) in the range of 70 to 100% and moisture content in the range of 10 to 80% (w/w) to the enzyme solution in step (a), while maintaining the pH in the range of 4 to 6 and temperature of 40 to 60° C., to obtain a initial reaction mixture containing a predetermined biomass:enzyme ratio, wherein the predetermined biomass:enzyme ratio in the initial reaction mixture is in the range of $1:10^4$ to $1:10^6$ (Kg of biomass/FPU of enzyme); adding remaining biomass in lots repeatedly as in step (b) over a period of 30 to 90 mins to obtain solid loading of 10 to 30% in the final reaction mixture, wherein biomass:enzyme ratio is maintained in the range of $1:10^3$ to $1:10^5$ (Kg of biomass/FPU of enzyme); allowing the final reaction mixture to react for an additional 5 to 120 mins to obtain a biomass hydrolysate, wherein 40 to 80% solubilization of biomass is achieved; separating solid-liquid contents of the biomass hydrolysate from step (d) to obtain a filtrate comprising soluble sugars and enzyme, and a residue of unhydrolysed biomass and adsorbed enzyme; separating the soluble enzyme from soluble sugars present in the filtrate; and recycling the residue from step (e) and the separated soluble enzyme from step (f) to step (b) to maintain the predetermined biomass:enzyme ratio for production of soluble sugars.

An aspect of the present invention provides for a process for enzyme mediated hydrolysis of pretreated biomass for production of soluble sugars in reactor vessel system. The strategies used for enzymatic saccharification are categorized into three main groups, i.e. (a) to increase the cumulative biomass in a reactor; (b) to recycle enzyme; (c) to mitigate inhibitory effect. Thus, the present invention enhanced total solid content result in production of soluble sugars

BRIEF DESCRIPTION OF THE DRAWING

The invention will be described further with respect to the following in which:

FIG. 1 depicts the process for gradual feed addition of biomass to achieve high substrate concentration. The process involves addition of feed at a steady interval to achieve a final solid loading of 15%. The resultant solubilized reaction mixture is subjected to ultrafiltration, to separate the retentate consisting of unhydrolysed residue and soluble enzymes, and the permeate consisting of soluble sugars. The term "feed portion" used herein refers to the batch of substrate added gradually to the reaction mixture. The term unhydrolysed residue used herein refers to the insoluble biomass left post solubilization which is recycled back into the reaction for further use.

DETAILED DESCRIPTION OF THE INVENTION

In the present invention, numbers of terms are used for description of invention. The definitions of terms are as follows:

Definitions:

The term "biomass" used herein refers to biomass comprises of corn cobs, corn stover, corn fiber, corn husks, sawdust, wheat straw, sugar cane bagasse, switchgrass, rice straw and grasses; and is suitably pretreated to obtain enriched holocellulose containing more than 70% and make the holocellulose amenable to enzymatic reaction.

The term "biomass hydrolysate" used herein refers to hydrolysis product comprising mixture of the hydrolysed biomass, enzyme and the unhydrolysed biomass from the reactor vessel.

The term "soluble sugars" used herein refers to all polysaccharides and monosaccharides, and their mixtures that are water soluble and can be used as carbon substrates by microorganisms in fermentation process to produce biofuels, biochemicals and/or also used as sugars in any food, pharma and/or other applications.

The term "heel" used herein refers to the initial liquid or slurry charged into a reactor before the introduction of the pretreated biomass and commencement of the of saccharification process.

The present invention relates to a process for enzyme mediated hydrolysis of biomass for production of soluble sugars, wherein the enzyme, enables cellulose solubilization to allow a high biomass loading for the hydrolysis reaction, can be recycled and can produce a biomass hydrolysate with high sugar concentrations.

One object of the present invention is to provide a process with enzyme recycling to obtain a high loading of the biomass, which produces a biomass hydrolysate with high sugars concentration.

Another object of the invention is to evaluate a substrate concentration to increase the loading of biomass during enzymatic hydrolysis with respect to cellulose conversion and decrease the viscosity during hydrolysis with aim of providing some insight into the interplay between biomass loading, viscosity, and enzyme-catalyzed cellulose degradation of biomass material.

Yet another objective of present invention is to provide recovery and recycling of the enzyme from biomass hydrolysate for further use in the enzymatic hydrolysis.

Another object of the invention is to provide a process to avoid substrate inhibition and end-product inhibition which play a vital role in conversion of biomass to soluble sugars.

One of the embodiment of the present invention provides a process for production of soluble sugars from biomass, wherein the said process comprises:

a. preparing an enzyme solution with pH in the range of 4 to 6 in a reactor vessel at a temperature in the range of 40 to 60° C.;

b. adding one lot of biomass with holocellulose % in the range of 70 to 100% and moisture content in the range of 10 to 80% (w/w) to the enzyme solution in step (a), while maintaining the pH in the range of 4 to 6 and temperature of 40 to 60° C., to obtain a initial reaction mixture containing a predetermined biomass:enzyme ratio, wherein the predetermined biomass:enzyme ratio in the initial reaction mixture is in the range of $1:10^4$ to $1:10^6$ (Kg of biomass/FPU of enzyme);

c. adding remaining biomass in lots repeatedly as in step (b) over a period of 30 to 90 mins to obtain solid loading of 10 to 30% in the final reaction mixture, wherein biomass:enzyme ratio is maintained in the range of $1:10^3$ to $1:10^5$ (Kg of biomass/FPU of enzyme);

d. allowing the final reaction mixture to react for an additional 5 to 120 mins to obtain a biomass hydrolysate, wherein 40 to 80% solubilization of biomass is achieved;

e. separating solid-liquid contents of the biomass hydrolysate from step (d) to obtain a filtrate comprising soluble sugars and enzyme, and a residue of unhydrolysed biomass and adsorbed enzyme;

f. separating the soluble enzyme from soluble sugars present in the filtrate; and g. recycling the residue from step (e) and the separated soluble enzyme from step (f) to step (b) to maintain the predetermined biomass:enzyme ratio for production of soluble sugars.

The present invention also provides a process for enzyme mediated hydrolysis of pretreated biomass for production of soluble sugars in reactor vessel system. The strategies used for enzymatic saccharification are categorized into three main groups, i.e. (a) to increase the cumulative biomass in a reactor; (b) to recycle enzyme; (c) to mitigate inhibitory effect. Thus, the present invention enhanced total solid content result in production of soluble sugars.

One of the most preferred embodiments of the present invention provides a process for production of soluble sugars by hydrolysis of biomass, wherein biomass used for hydrolysis process is agricultural product selected from, but not limited to, the group comprising of corn cobs, corn stover, corn fiber, corn husks, sawdust, wheat straw, sugar cane bagasse, switchgrass, rice straw and grasses; and suitably pretreated to make the cellulose and hemicelluloses content amenable to enzymatic reaction.

According to yet another embodiment of the present invention the biomass-used for hydrolysis process may be pretreated to obtain enriched holocellulose containing more than 70% and make the holocellulose amenable to enzymatic reaction According to another embodiment of present invention biomass may be pretreated by any method known to one skilled in the art such as with acid, base, organosolvent, oxidizing agents or other chemicals and/or in combination with steam or with steam alone, mechanical disruption such as by crushing, grinding, or chopping.

In yet another embodiment of the present invention provides for a process for production of soluble sugars from pretreated biomass, wherein the pretreated biomass is subjected to multiple size reduction steps before hydrolysis process, and the reactor contents are mixed thoroughly allowing pH and temperature control during hydrolysis.

According to yet another embodiment of present invention the combination of size reduction, faster enzymatic hydrolysis and addition of biomass in a steady manner, allows efficient mixing of biomass thereby resulting in reduced biomass viscosity build up. The size reduction steps allow rapid solubilization of the wet solid biomass.

In the present invention, the sequential loading of pretreated biomass as substrate during enzymatic hydrolysis is carried out for production of soluble sugars. The reaction is subjected to gradual loading of substrate to increase the substrate levels from 10 to 30% Dry Mass (DM) (w/w). The highest final glucose concentration, is in the range of 50 to 150 gm/liter after 2 hrs.

Another embodiment of present invention provides a process for biomass loading, wherein the biomass is loaded initially into the reactor vessel as mixable slurry of a particular concentration ranging from 1% to 10%.

According to yet another embodiment of present invention, the biomass in initial loading biomass is added steadily in two, three, four, five, six, seven, nine, ten and twelve feed portions within 0.5 to 1.5 hrs to increase the solid loading at least about 30% (w/v).

In another embodiment of present invention, the biomass is added steadily in three to nine feed portions within 0.5 to 1.0 hrs to increase the solid loading at least about 15% (w/v).

In yet another embodiment of the present invention there is provided a process for production of soluble sugars from biomass, wherein feed time is about. 0.5 to 1.5 hrs.

In yet most preferred embodiment of the present invention the portion of total biomass to be added in reaction mixture is done in one portion and/or lots at every 2.5 to 50 mins to achieve the predetermined solid biomass loading in the range of 10% to 30% and predetermined total feed time in between 0.5 to 1.5 hrs.

In another embodiment of the present invention provides for a process for production of soluble sugar from biomass, wherein addition of biomass to the enzyme solution is carried out steadily under stirring with overhead stirrer having stirring capacity in the range of 200 rpm to 400 rpm, allowing complete biomass mixing resulting in lower biomass viscosity and uniform pH and temperature control during hydrolysis process.

In most preferred embodiment of the present invention, all saccharification enzymes are added at the beginning of the reaction.

According to another embodiment of the present invention, the saccharification enzymes used for hydrolysis is selected from the group consisting of cellulases, peptidases, lipases, ligninases and feruloyl esterases and additional ancillary enzymes, most preferably cellulases.

In one embodiment of the invention, enzyme is added to the reaction system at a protein loading ranging from about 2 mg/g to about 95 mg/g of biomass.

In yet another embodiment of the present invention, biomass present in the reactor vessel from the beginning of the hydrolysis process is in the form of mixable slurry which become substantially homogenous under the action of the agitated system and less viscous under the action of saccharifying enzymes concentration.

In accordance of the present invention, the complete biomass mixing provides better pH and temperature controllability, resulting in biomass hydrolysate with high dry weight biomass with high yields of soluble sugars.

In a preferred embodiment of the present invention, incubation of initial reaction mixture is carried out at temperature in the range of 40 to 60° C. and at pH in the range of 4 to 6 for a period of 2.5 to 120 mins Another embodiment of the present invention, the partially hydrolyzed biomass in the slurry may become less viscous, allowing additional biomass to be added to the slurry while maintaining sufficient mixability and viscosity of the slurry with increase in the per cent of total solids loaded in the hydrolyzing slurry.

According to yet another embodiment of the invention, the hydrolysis of biomass is performed at a pH in the range of 4 to 6 and temperature optima ranging from 40° C. to 60° C. to achieve 40 to 80% solubilization of biomass.

In accordance of the present invention the desired temperature ranging from 40° C. to 60° C. may be achieved by heating of the biomass slurry based on the temperature optima for the saccharification enzymes to be used and the particular type of biomass being processed, to achieve the best possible saccharification reaction rate.

The desired pH of the slurry is brought through by addition of acid or base as required while mixing of the biomass slurry to ensure that a substantially uniform pH is achieved throughout the biomass material.

In yet most preferred embodiment of the present invention, pH control of the slurry is adjusted by using acid and/or base, the acid is selected from group consisting of HCl, $H_2SO_4$, $CH_3COOH$, $H_3PO_4$, $HNO_3$, or base is selected from the group consisting of NaOH, KOH, NH3, $Na_2CO_3$, and $K_2CO_3$.

One of the embodiments of the invention provide for a process for hydrolysis of biomass, wherein the biomass hydrolysate obtained from hydrolysis process contains mixture of soluble sugar solution, enzyme and unhydrolysed biomass.

In accordance to the present invention the process described is such that the biomass hydrolysis such that maximum enzyme remains adsorbed on the biomass and generates concentrated sugars stream.

Another embodiment of the present invention, the separation or filtration of enzyme and/or unhydrolysed biomass from hydrolysate is carried out using Microfiltration (MF), the membrane having molecular weight cut-off (MWCO) of 100 kDa to 500 kDa.

Another embodiment of the present invention, the recovery and recycling of cellulase enzyme through separation of the soluble sugar solution and cellulase enzyme from retentate obtained after Ultra-filtration is carried out using membrane having molecular weight cut-off (MWCO) of 1 kDa to 20 kDa.

The portion of biomass slurry that remains unhydrolysed, and the substantial amount of enzyme adsorbed onto it is recycled. The additional enzyme present along with the soluble sugars in the hydrolysate is recovered by filtration and recycled.

According to another embodiment of the present invention, the biomass is converted into soluble sugars in 1 to 4 hrs.

The permeate obtained after ultra filtration comprises soluble sugars may be transferred to a fermentation process.

One of the most preferred embodiments of the present invention, the concentration of soluble sugars in the hydrolysate produced in the present process is at least 75 g/L that is typically considered to be high sugar concentration.

According to yet another embodiment of the present invention soluble sugars produced by the process of the invention may be used in fermentation process to produce valuable products such as fuels and other chemicals, including ethanol.

Advantages of Present Invention
1) The present invention has several economic advantages over conventional batch process such as lowering capital cost due to reduced volume, lower operating cost and lower down-stream processing cost due to higher product concentration.
2) The provided process is more effective leading to more rapid viscosity reduction and more efficient production of soluble sugars than the traditional known processes.
3) Although use of enzyme for hydrolysis process is expensive but present invention provides recovery and recycling of used enzyme that makes the process more cost effective and continuous for production of soluble sugars from biomass.
4) The present invention provides a process for enzyme adsorption on the biomass prior to hydrolysis which leads to increase reaction rate and enzyme recovery.

Following examples are given by the way of illustration of the present invention and not intended to limit the scope of the present invention.

EXAMPLES

Example 1

Saccharification of Biomass with Varying Cellulose Content

Pretreated biomass consisting of varying holocellulose content (70-95%) derived by acid/alkali treatment of wheat straw was solubilized in an enzyme solution maintained at 50° C. and pH of 5.0 with total dry solid loading of 15.0%. The initial heel consisting of 37.5 g of biomass on dry basis was mixed with an enzyme solution composed of Cellulase B™ (Advanced Enzyme Technology Ltd., Thane, India) and 750 gm of acidified water at a protein loading of 27.75 mg/g of biomass. The reaction mass was stirred at 300 rpm and temperature maintained to 50° C. and pH to 5.0. The remaining biomass was added gradually within 0.5-1.0 hr to increase the solid loading to 15%. The percentage of holocellulose solubilized was determined as reduction in dry weight of the total holocellulose added in the reaction and represented in terms of % solubilization as given below:

$$\% \text{ Solubilization} = \frac{\text{Dry weight of unhydrolyzed holocellulose at the end of reaction}}{\text{Dry weight of total holocellulose added in the reaction}} \times 100$$

TABLE 1

Saccharification of biomass with varying cellulose content

| Example no. | Biomass loading | Holocellulose content | % Solubilization |
|---|---|---|---|
| 1 | 15% | 80% | 35.75% |
|   |     | 85% | 58.16% |
|   |     | 95% | 71.50% |

Example 2

Saccharification of Biomass with Varying Biomass Loading

Pretreated biomass consisting of holocellulose content (70-95%) derived by acid/alkali treatment of wheat straw was solubilized in an enzyme solution maintained at 50° C. and pH of 5.0 with different total dry solid loading of 15.0%, 20.0% and 30.0%. The initial heel consisting of 37.5 g of biomass on dry basis was mixed with an enzyme solution composed of Cellulase B™ (Advanced Enzyme Technology Ltd., Thane, India) and 750 gm of acidified water at a protein loading of 27.75 mg/g of biomass. The reaction mass was stirred at 300 rpm and temperature maintained to 50° C. and pH to 5.0. The remaining biomass was added gradually within 0.5-1.0 hr to increase the solid loading to 15.0%, 20.0% and 30.0%. Percent solubilization was determined as mentioned earlier in Example 1.

TABLE 2

Saccharification of biomass with varying biomass loading

| Example no. | Biomass loading | Holocellulose content | % Solubilization |
|---|---|---|---|
| 2 | 15% | 95% | 71.50% |
|   | 20% | 95% | 58.13% |
|   | 30% | 95% | 52.78% |

Example 3

Saccharification of Pretreated Biomass

Pretreated biomass derived by acid/alkali treatment of wheat straw was solubilized in an enzyme solution maintained at 50° C. and pH of 5.0 with total dry solid loading of 15%. The initial heel consisting of 37.5 g of biomass on dry basis was mixed with an enzyme solution composed of Cellulase B™ (Advanced Enzyme Technology Ltd., Thane, India) and 750 gm of acidified water at a protein loading of 27.75 mg/g of biomass. The reaction mass was stirred at 300 rpm and temperature maintained to 50° C. and pH to 5.0. The remaining biomass was added gradually within 0.5-1.0 hr to increase the solid loading to 15%. Percent solubilization was determined as mentioned earlier in Example 1.

TABLE 3

Saccharification of pretreated biomass by Cellulase B

| Example No. | Biomass Component | Biomass Type | Enzyme | pH | % Solubilization |
|---|---|---|---|---|---|
| 3 | Cellulose | Wheat Straw | Cellulase B | 5.0 | 73.14 |
|   | Holocellulose |   |   |   | 62.14 |

Example 4

Feed Portions on Biomass Solubilization (~85% Holocellulose)

100 gm (dry mass) of pre-treated biomass (~85% holocellulose) is added to 2L of enzyme solution maintained at 50° C. and pH 5.0 to obtain a substrate: enzyme ratio of $1:10^6$ (Kg of biomass/FPU of enzyme). Gradual additions of 200 gm of pre-treated biomass are carried out in three, five, seven and nine feed portion over the next one hour to obtain a substrate: enzyme ratio of $1:10^5$ (Kg of biomass/FPU of enzyme). The reaction is allowed to proceed for an hour at the above conditions. The entire reaction mix is centrifuged to separate solid residue from the solubilised mass, which is further subjected to membrane filtration to separate the sugars and enzyme. Percent solubilization was determined as mentioned earlier in Example 1. Following table shows % solubilisation that can be achieved:

TABLE 4

Effect of feed portions on biomass solubilization (~85% holocellulose)

| Example no. | Biomass loading | Feed Portions | % Solubilization |
|---|---|---|---|
| 3 | 15% | 3 | 56.76% |
|   |   | 5 | 62.14% |
|   |   | 7 | 65.50% |
|   |   | 9 | 68.30% |

Example 5

Feed Portions on Biomass Solubilization (~92% Cellulose)

100 gm (dry mass) of pre-treated biomass (~92% cellulose) is added to 2L of enzyme solution maintained at 50° C. and pH 5.0 to obtain a substrate: enzyme ratio of $1:10^6$ (kg of biomass: FPU of enzyme). Gradual additions of 200 gm of pre-treated biomass are carried out in three, five, seven and nine feed portion over the next one hour to obtain a substrate:enzyme ratio of $1:10^5$ (Kg of biomass/FPU of enzyme). The reaction is allowed to proceed for an hour at the above conditions. The entire reaction mix is centrifuged to separate solid residue from the solubilised mass, which is further subjected to membrane filtration to separate the sugars and enzyme. Percent solubilization was determined as mentioned earlier in Example 1.Following table shows % solubilisation that can be achieved:

TABLE 5

Effect of feed portions on biomass solubilization (~92% cellulose)

| Example no. | Biomass loading | Feed Portions | % Solubilization |
|---|---|---|---|
| 5 | 15% | 3 | 65.51% |
|   |   | 5 | 72.80% |
|   |   | 7 | 75.98% |
|   |   | 9 | 79.58% |

Example 6

Particle-size for Biomass Solubilization

Rice straw was size reduced and subjected to alkali pre-treatment for holocellulose (>80% cellulose). The above pre-treated sample is added to an enzyme solution maintained at 50° C. and pH 5.0 to make an initial concentration of 5%. Slow additions of pretreated biomass are carried out over the next one hour to build up the biomass concentration to 15%. The reaction is allowed to proceed for another hour at the above conditions. The entire reaction mix is centrifuged to separate solid residue from the solubilised mass, which is further subjected to membrane filtration to separate the sugars and enzyme. Percent solubilization was determined as mentioned earlier in Example 1. Following table shows % solubilisation that can be achieved:

TABLE 6

Effect of particle size on biomass solubilization

| Example no. | Biomass loading | Biomass size | % Solubilization |
|---|---|---|---|
| 6 | 15% | 1 mm | 68.17% |
|   | 15% | 0.4 mm | 73.14% |
|   | 15% | 0.05 mm | 35.60% |

Example 7

Comparison of Batch and Fed-batch Cellulose Hydrolysis 300 gm (dry mass) of pre-treated biomass (>80% cellulose) is added to 2L of enzyme solution maintained at 50° C. and pH 5.0 in two different modes of reaction a) single addition-batch and b) gradual additions over an hour—fedbatch. The reaction is allowed to proceed for an hour at the above conditions. The entire reaction mix is centrifuged to separate solid residue from the solubilised mass, which is further subjected to membrane filtration to separate the soluble sugars and enzyme. Percent solubilization was determined as mentioned earlier in Example 1. Following table shows % solubilisation that can be achieved:

TABLE 7

Biomass solubilisation—comparison in modes of operation

| Example no. | Biomass loading | Mode of Operation | % Solubilization |
|---|---|---|---|
| 7 | 15% | Batch | 25.98% |
|   |     | Fed Batch | 62.37% |

Example 8

Effect of Enzyme Loading on Biomass Hydrolysis 100 gm (dry mass) of pre-treated biomass (>80% cellulose) is added to 2L of enzyme solution containing different protein loading to obtained substrate:enzyme ratio from $1:10^4$ to $1:10^7$ (Kg of biomass/FPU of enzyme). The reaction was carried out at 50° C. and pH 5.0. Slow additions of 200 gm of pretreated biomass are carried out over the next one hour to build up the biomass concentration to 15% and the reaction is allowed to proceed for another hour at the above conditions. The entire reaction mix is centrifuged to separate solid residue from the solubilised mass, which is further subjected to membrane filtration to separate the sugars and enzyme. Percent solubilization was determined as mentioned earlier in Example 1. Following table shows % solubilisation that can be achieved:

TABLE 8

Effect of enzyme loading on biomass solubilization

| Example no. | Biomass loading | Enzyme Load (Kg of biomass/FPU of enzyme) | Feed portion | % Solubilization |
|---|---|---|---|---|
| 8 | 15% | $1:10^4$ | 5 | 18.45% |
|   |     | $1:3 \times 10^4$ |   | 32.14% |
|   |     | $1:4 \times 10^4$ |   | 54.35% |
|   |     | $1:6 \times 10^4$ |   | 62.37% |
|   |     | $1:10^5$ |   | 68.14% |

Example 9

Continuous Hydrolysis of Holocellulose (~85% Holocellulose) with Enzyme Recycle 100 gm (dry mass) of pre-treated biomass (~85% holocellulose) is added to 2L of enzyme solution maintained at 50° C. and pH 5.0 to obtain a substrate: enzyme ratio of $1:10^6$ (Kg of biomass/FPU of enzyme). Gradual additions of 200 gm of pre-treated biomass are carried out over the next one hour to obtain a substrate:enzyme ratio of $1:10^5$ (Kg of biomass/FPU of enzyme). The reaction is allowed to proceed for an hour at the above conditions. The entire reaction mix is centrifuged to separate solid residue from the solubilised mass, which is further subjected to membrane filtration to separate the sugars and enzyme. The solid residue and the soluble enzyme was recycled back and 150 g of fresh biomass was gradually added over next one hour to obtain a substrate:enzyme ratio of $1:10^5$ (Kg of biomass/FPU of enzyme). The entire reaction mixture is again subjected to centrifugation and membrane filtration to obtained solid residue and soluble enzyme which is again recycled back over a period of three consecutive cycles. Percent solubilization was determined as mentioned earlier in Example no.1.

TABLE 9

Continuous hydrolysis of holocellulose with enzyme recycles

| Example no. | Cycle no. | Biomass Loading % (w/w) | Enzyme loading (Kg of biomass/FPU of enzyme) | Reaction time (h) | % Solubilization |
|---|---|---|---|---|---|
| 9 | 1 | 15% | $1:10^5$ | 2 | 61.8% |
|   | 2 |     | Recycled Enzyme | 2 | 48.15% |
|   | 3 |     | Recycled Enzyme | 2 | 42.86% |
|   | 4 |     | Recycled Enzyme | 2 | 47.24% |

Example 10

Substrate:Enzyme Ratios in Reaction Mix 300 gm (dry mass) of pre-treated biomass (>80% holocellulose) is added to 2L of enzyme solution in different substrate:enzyme ratios from ($1:10^2$ to $1:10^7$) maintained at 50° C. and pH 5.0 in five gradual additions over 1.5 hr. The reaction is stirred for an hour at the above conditions. The entire reaction mix is filtered through a nylon mesh to separate solid residue from the solubilised mass, which is further subjected to membrane filtration (micro+ultra) to separate the soluble sugars and enzyme. Percent solubilization was determined as mentioned earlier in Example 1. Following table shows % solubilisation that can be achieved:

TABLE 10

Effect of substarte:enzyme ratio on biomass solubilization

| Example no. | Enzyme Load (Kg of biomass/FPU of enzyme) | Feed portion | % Solubilization |
|---|---|---|---|
| 10 | $1:10^2$ | 5 | 0.86% |
|    | $1:10^3$ |   | 5.34% |
|    | $1:10^4$ |   | 17.90% |
|    | $1:10^5$ |   | 67.87% |
|    | $1:10^6$ |   | 75.14% |
|    | $1:10^7$ |   | 83.52% |

Example 11

Enzyme Reuse for Solubilization of Holocellulose (>95% Holocellulose)

300 gm (dry mass) of pre-treated biomass (>95% holocellulose) is added to 2L of enzyme solution maintained at 50° C. and pH 5.0 in five gradual additions over 1.5 hr. The reaction is stirred for an hour at the above conditions. The entire reaction mix is filtered through a nylon mesh to separate solid residue from the solubilised mass, which is further subjected to membrane filtration (micro+ultra) to separate the soluble sugars and enzyme. The enzyme solution recovered after membrane filtration is mixed with the solid residue obtained after filtration. New portions of pre-treated biomass are now added to the mixture to make up 15% solid loading. The above scheme of operations is repeated for five cycles. Percent solubilization was determined as mentioned earlier in Example 1. Following table shows % solubilisation that can be achieved in each cycle:

TABLE 11

Reuse of enzyme for biomass solubilization

| Example no. | Enzyme Recycle | Feed portion | % Solubilization |
|---|---|---|---|
| 11 | 1 | 5 | 82.31 |
|  | 2 |  | 75.10 |
|  | 3 |  | 72.34 |
|  | 4 |  | 70.23 |
|  | 5 |  | 68.23 |

Example 12

Soluble Enzyme Recycle for Biomass Solubilization 450 gm (dry mass) of pre-treated biomass (>85% holo-cellulose) is added to 2L of enzyme solution maintained at 50° C. and pH 5.0 in five gradual additions over 1.5hr. The reaction is stirred for an hour at the above conditions. The entire reaction mix is filtered through a nylon mesh to separate solid residue from the solubilised mass, which is further subjected to membrane filtration (micro+ultra) to separate the soluble sugars and enzyme. The enzyme solution recovered after membrane filtration is diluted in fresh acidified buffer to 2L. New portions of pretreated biomass are now added to the enzyme solution to make up 15% solid loading. The above scheme of operations is repeated for five cycles. Percent solubilization was determined as mentioned earlier in Example I. Following table shows % solubilisation that can be achieved in each cycle:

TABLE 12

Soluble enzyme recycled for biomass solubilization

| Example no. | Enzyme Recycle | Feed portion | % Solubilization |
|---|---|---|---|
| 12 | 1 | 5 | 68.21 |
|  | 2 |  | 45.10 |
|  | 3 |  | 22.34 |
|  | 4 |  | 10.23 |
|  | 5 |  | 2.31 |

Example 13

Cellulose Solubilization by Varying Enzyme Concentration (mg/g of Biomass)

Cellulose derived by alkali treatment of Wheat Straw at 50° C. and pH of 5.0 with dry solid loading of 15.0% was used for the reaction. The initial heel consisted of 1000 g of water (pH 5) and 37.5 g of Cellulose. Reaction mass was stirred at 300 rpm. Temperature was maintained to 50° C. and pH to 5.0. Enzyme added to the reaction system was Cellulase B™(Advanced Enzyme Technology Ltd., Thane, India) at a protein loading of 4.625 mg/g, 11.56 mg/g, 18.5 mg/g, 27.75 mg/g and 46.25 mg/g of biomass. Following liquefaction, remaining biomass was added gradually in five feed portions within 1.0-1.5 hr to increase the solid loading to 15%. Sugars content in the reaction mass was determined by protocols for sugars measurement (Ghose etal, Measurement of cellulase activity. Pure and Applied Chemistry, 59(2) 257-268, 1988). Amount of glucose released increases with enzyme load, indicated in Table 13.

TABLE 13

Varying enzyme concentration on solublization of cellulose

| Example No. | Enzyme Load, mg/g | No. of Feed Portion | % soluble sugars |
|---|---|---|---|
| 13 | 4.62 | 5 | 0.41 |
|  | 11.56 |  | 2.84 |
|  | 18.50 |  | 3.00 |
|  | 27.75 |  | 4.10 |
| 13 | 46.25 | 5 | 5.50 |

We claim:

1. A process for production of soluble sugars from biomass comprising:
    a. preparing an enzyme solution with pH in the range of 4 to 6 in a reactor vessel at a temperature in the range of 40 to 60° C.;
    b. adding one lot of biomass with holocellulose % in the range of 70 to 100% and moisture content in the range of 10 to 80% (w/w) to the enzyme solution in step (a), while maintaining the pH in the range of 4 to 6 and temperature of 40 to 60° C., to obtain a initial reaction mixture containing a predetermined biomass:enzyme ratio, wherein the predetermined biomass:enzyme ratio in the initial reaction mixture is in the range of $1:10^4$ to $1:10^6$(Kg of biomass/FPU of enzyme);
    c. adding remaining biomass in lots repeatedly as in step (b) over a period of 30 to 90 mins to obtain solid loading of 10 to 30% in the final reaction mixture, wherein biomass:enzyme ratio is maintained in the range of $1:10^3$ to $1:10^5$ (Kg of biomass/FPU of enzyme);
    d. allowing the final reaction mixture to react for an additional 5 to 120 mins to obtain a biomass hydrolysate, wherein 40 to 80% solubilization of biomass is achieved;
    e. separating solid-liquid contents of the biomass hydrolysate from step (d) to obtain a filtrate comprising soluble sugars and enzyme, and a residue of unhydrolysed biomass and adsorbed enzyme;
    f. separating the soluble enzyme from soluble sugars present in the filtrate; and
    g. recycling the residue from step (e) and the separated soluble enzyme from step (f) to step (b) to maintain the predetermined biomass:enzyme ratio for production of soluble sugars.

2. The process as claimed as claim 1, wherein the said biomass is agricultural product selected from, the group consisting of: corn cobs, corn stover, corn fiber, corn husks, sawdust, wheat straw, sugar cane bagasse, switchgrass, rice straw and grasses; and suitably pretreated to enrich holocellulose to >70% and make the holocellulose amenable to enzymatic reaction.

3. The process as claimed in claim 1, wherein the said enzyme is selected from the group consisting of: cellulases, peptidases, lipases, ligninases and feruloyl esterases.

4. The process as claimed in claim 1, wherein the said enzyme solution is prepared in reactor vessel at a protein loading of from about 2 mg/g to about 95 mg/g of biomass.

5. The process as claimed in claim 1, wherein the said biomass is loaded initially into the reactor vessel as mixable slurry having concentration in the range of 1 to 10% (w/v).

6. The process as claimed in claim 1, wherein the remaining biomass is added steadily in two, three, four, five, six, seven, nine, ten and twelve feed portions within 0.5 to 1.5 hrs to increase the solid loading at least 30% (w/v).

7. The process as claimed in claim 1, wherein the biomass is added steadily in three to nine feed portions within 0.5 to 1.0 hrs to increase the solid loading at least 15% (w/v).

8. The process as claimed in claim 1, wherein the final biomass:enz-yme ratio is in the range of $1:10^3$ to $1:10^5$ (Kg of biomass/FPU of enzyme).

9. The process as claimed in claim 1, wherein the concentration of soluble sugars in the biomass hydrolysate is at least 75 g/L of total soluble high concentration sugars.

10. The process as claimed in claim 1, wherein said biomass is converted into soluble sugars in 0.5 to 2 hrs.

11. The process as claimed in claim 1, wherein said soluble sugars comprise polysaccharides and monosaccharides.

12. The process as claimed in claim 1, wherein the highest final glucose concentration in soluble sugars is obtained in between 50 to 150 g/L.

\* \* \* \* \*